United States Patent [19]

Aroonsakul

[11] Patent Number: 4,791,099

[45] Date of Patent: Dec. 13, 1988

[54] METHOD OF TREATMENT FOR CENTRAL NERVOUS SYSTEM DISEASES SUCH AS ALZHEIMER'S DISEASE AND PARKINSON'S DISEASE

[76] Inventor: Chaovanee Aroonsakul, 505 N. Lake Shore Dr., Ste. 3006, Chicago, Ill. 60611

[21] Appl. No.: 666,254

[22] Filed: Oct. 29, 1984

[51] Int. Cl.⁴ .................. A61K 37/00; A61K 31/56; A61K 35/55
[52] U.S. Cl. .................................. 514/2; 514/171; 424/108
[58] Field of Search ............... 514/182, 178, 2, 171; 424/108

[56] References Cited

U.S. PATENT DOCUMENTS 4,469,707  9/1984  Lindberg .......................... 424/330

OTHER PUBLICATIONS

Merck Index (1983), 10th Edition, #8562.
Chemical Abstracts, vol. 86 (1977) #50823s; Cotzias et al.

*Primary Examiner*—Leonard Schenkman
*Assistant Examiner*—Joseph A. Lipovsky

[57] ABSTRACT

A method of treating humans suffering from central nervous system diseases, such as Alzheimer's disease, cerebral atrophy, Parkinson's disease, senile tremor, essential tremor, and cerebellar atrophy, as well as diseases where dementia is present. The treatment consists of inducing into the patient's blood stream at least one from the group consisting of: sex hormones and anabolic hormones. Ergolid myselates may be used in conjunction with the hormone, as well as a vasodilator and non-steroid anti-inflammatory. Growth hormone may also be used in those patients in advanced stages of the disease, or in those patients where it has been determined that a low level of growth hormone is present.

4 Claims, No Drawings

METHOD OF TREATMENT FOR CENTRAL NERVOUS SYSTEM DISEASES SUCH AS ALZHEIMER'S DISEASE AND PARKINSON'S DISEASE

BACKGROUND OF THE INVENTION

The present invention is directed to a method of treatment for central nervous system diseases. These diseases for which the present inventive method has been found useful are: Alzheimer's disease; Parkinson's disease; essential tremor; senile tremor; and cerebellar atrophy and cerebral atrophy. Each of these has been found to affect different portions of the brain. Alzheimer's disease affects the portion of the brain vital to memory retention, the cortex. It is generally believed that the disease cuts off the cholinergic pathways by deficiencies of the enzyme choline acetyltranspherase, which is the chemical messenger from the nucleus basalis to the cortex. Parkinson's disease is known to affect the nerve cells of the basal ganglia. Cerebellar atrophy is known to affect the nerve cells of the cerebellum. It has also been determined that in each of the above diseases, intrinsic depression develops, which is usually associated with an entirely different portion of the brain than those affected by the above-named diseases. It is generally known that the cerebellar and extra-pyrimadal tract portions of the brain are directly associated with senile tremor and essential tremor. It is also known that in each of these diseases characterized by biochemical lesions in enzymes, membranes, or structure proteins of particular components, cellular atrophy is the result, which is a slow process of cellular deterioration, sometimes deferred by repair processes, but leading to cellular atrophy, and eventually resulting in serious functional loss, causing the symptoms associated with each of the diseases. Such cellular atrophy generally occurs with advancing age, but, owing to these diseases, the processes are somehow speeded up, in a manner not known or understood at the present time. What is certain, however, is that in any cellular break-down, the enzymes required for protein synthesis are lacking. Further, it is also apparent that this lack of enzyme formation, and concomitant lack of protein synthesis, are caused by some interruption in the neural network through which biochemical signals are generated and transported. Thus, the very problem of each of these diseases runs to the basic structure of life: To wit, RNA and DNA, which program each cell to provide the necessary enzymes for life-sustaining activity.

Heretofore, there has been no effective method of treatment of each of the above-named diseases. In the case of Parkinson's disease, L-Dopa has been employed and has achieved some success. However, the period of efficacy of L-Dopa is limited to a few months, after which all of its beneficial effects disappear leaving only contraindication. In the case of Alzheimer's disease, and the remainder of the above-named diseases, ergoloid myselates have been used to some small success, but only in a very limited way, and have been successful only for a short time period. Further, ergoloid myselates suffer from the disadvantage of also causing unwanted side effects, that are often dangerous to the health and well-being of the patient. Just how this drug works is not known at this time, but it does offer some relief, though only temporary, to help restore mental acuteness, awareness and faculty.

SUMMARY OF THE INVENTION

The present invention consists of a method of treating patients suffering from the above-named diseases with the hormones: sex hormones and anabolic hormones. For male patients, androgens are used, or suitable anabolic hormone substitutes are used. For female patients, estrogens are used in combination with androgens or anabolic hormones. For both male and female patients, additional drugs may be used to ensure that the induction of hormone into the blood stream is effected, so that the hormone or hormones are delivered to the site of the brain causing the dysfunction and symptoms. Thus, nonsteroidal antiinflammatory drugs and vasodilaters may be used in combination with the hormone treatment to ensure that the blood delivers the hormone or hormones to the brain. Further, the hormone method of treatment may be supplemented with growth hormones, which are known for their anabolic tendencies, especially in those cases where there has been detected a noticeable loss of such growth hormone in the patient's system, which growth hormones also exhibit remarkable rejuvenating properties.

DETAILED DESCRIPTION OF THE INVENTION

To reverse the degenerative nature of central nervous disorder diseases, such as Parkinson's disease, Alzheimer's disease, senile tremor, and the like, and diseases especially associated with dementia, it has been discovered that treatment methods utilizing the synthesizing, metabolic effects of androgens, estrogens, and anabolic hormones have reversed the degenerative nature of the diseases, and have restored patients suffering from the diseases to more normal and productive lives, with the alleviation of many of the symptoms of the diseases. Further, upon continual and prolonged treatment with the above-named group of hormones, there has not been found any diminution of efficacy of the treatment, nor any serious contraindications and adverse side effects that would tend to discourage such treatment.

In one patient suffering from diagnosed Alzheimer's disease and early stage Parkinson's disease, which patient was sixty years old and weighed one-hundred eighty pounds, he was given 10 mg. of fluoxymesterone USP daily. In conjunction with the fluoxymesterone, the patient was given 1 mg. of ergolid myselates four times a day; 50 mg. of dipyridamole, four times a day; and acetyl salicylic acid enteric coated, four times a day, all taken orally. Within one week of the start of this treatment, the patient experienced noticeable improvement, including the cessation of Parkinsonism tremor, and a wider span of attentiveness. In about one month from the start of the treatment, the patient stopped bed-wetting, and was able to concentrate on television, and other mentally-stimulating activities. Within about two months, the patient's intellectual capacity increased so that he could carry on a conversation with another person. Within about three months, the patient was able to dress himself, and take a bath by himself. Within about four months, the patient was able to smile, and laugh occasionally. Within about five months, the patient was able to retain in his memory recent occurrences and happenings. When the above-described treatment and medicine was eliminated, the patient regressed, starting to revert back to the original condition before the treatment with the fluoxymesterone was begun. After resumption of the treatment with fluoxymesterone, with the other drugs above-named, and in their previously-given doses, the patient again responded and started to recover from the degenerative nature of the diseases.

In the treatment of central nervous system disorders, and especially those where dementia is present, it has been found that treating patients with the following hormones has caused alleviation of the degenerative nature of the diseases, and has resulted in putting the patient back on the road toward normalcy. These hormones belong to the group: Androgens for male patients; androgen-estrogen combination for female patients; anabolic hormones for either male or female patients; or a combination of any of the three classes within this group.

In the above-cited case history of one male patient who was treated with the androgen fluoxymesterone, in synthetic form, any of the following other androgens could have been used in lieu of, or in conjunction with, the fluoxymesterone: Testesterone; methyltesterone; and oxymethone. Furthermore, the patient could have been treated with any of the following anabolic hormones in lieu of the androgen, or in combination therewith: Oxymetholone; oxandrolone; ethylestrenol; stanozolol; nandolone; phenpropionate; decanoate; and methandriol. Whereas in the case of using the fluoxymesterone, a daily dosage of 10 mg. was provided the patient, in the case of the use of other androgens, either singly or in combination with another androgen, the precise dose could vary. However, the variations that would occur are directly dependent upon the anabolic effect of each of the types of androgens used. However, it has been found that a minimum dose of 1 mg. of any type of androgen above-named is preferred. Below such level, the beneficial results above-noted would likely not occur.

Further, combinations of anabolic hormones alone, or anabolic hormones with androgens, may also be used to find the precisely-desired anabolic effect to be had on the central nervous system of the patient, again with the minimum daily dosage of 1 mg., either for combinations, or individually-administered hormones.

Since a patient suffering from the diseases of the central nervous system, for which the treatment of the present invention has proven successful, also suffers from other ailments, either because these diseases strike primarily those advanced in age or because of other factors, it has been found necessary to also treat the patient with other drugs in order to ensure that the hormone used is adequately and safely delivered into the blood stream of the patient, and to the site in the brain affected by the disease, so as to act on the degenerative nerve cells. Toward this end, as shown by the above-cited case, the patient is typically treated also with vasodilater and non-steroidal anti-inflammatory drugs, to ensure that the hormone is delivered to the brain. Further, ergoloid myselates are also used, the use of which for dementia has been known in the art. Among vasodilaters, any of the following group may be used, either singly, or in combination: Dipyridamole; cyclospasmol; nylidinhydrochloride; papavarine hydrochloride; and isoxsuprine hydrochloride. Further, any well-known vasodilater may be used, the above being given only by way of example. For non-steroidal anti-inflammatory drugs, any of the following may be used singly or in combination: Aspirin; ibuprofen, indomethacin; tolmetin sodium; and piroxicam. Also, any other well-known non-steroidal anti-inflammatory drug may be used, the above being given only by way of example.

In the case of female patients, it is necessary to provide, in addition to the above-drugs and hormones, an estrogen. Since estrogens have little anabolic effect, and since, to provide ample anabolic effect, it is most often necessary to give a female patient an androgen and an estrogen, the estrogen is usually given to offset the masculinizing effects of the androgen.

Thus, in one case history of a female patient 78 years of age, weighing approximately one-hundred fifty pounds, diagnosed as having Alzheimer's disease, the patient was given the following, orally: 1.25 mg. conjugated estrogen once a day; 10 mg. methyltestesterone once a day; 1 mg. ergoloid myselate USP four times a day; 50 mg. dipyridamole four times a day; and 300 mg. acetyl salicylic acid enteric coated four times a day.

The ergolid myselate helps, it is believed in the art, to prevent the cell's temporary loss of protein; the dipyridamole increases cerebral blood flow; and the acetyl salicylic acid helps to prevent clots among other beneficial results. Just as in the case of the male patient noted above, this female patient experienced marked and fast rejuvenation, dissipation of dementia, increased mental alertness, and a general vitalization such that many of her Alzheimer disease symptoms disappeared.

Besides the use of conjugated estrogen, any estrogen from the following group may be used singly or in combination: Estradiol; estrone; estriol. Further, gonadotropins and chorionic gonadotropins may also be used, singly or in combination. Also, another androgen or an anabolic hormone could have been used successfully instead of the methyltestesterone.

In conjunction with the above-disclosed treatment, in these patients where it has been determined that the level of growth hormone in their system is below normal for their size, sex, and age bracket, the above-administering of drugs is supplemented with a growth hormone to re-establish normal levels thereof in the patients. These growth hormones, also of anabolic efficacy, serve to restore body function to a state receptive to treatment of the present invention in those cases where growth hormone levels are deficient. Further, the growth hormone may also be used in those patients having normal levels thereof, if it has been found that treatment with the androgen or anabolic hormones alone or in combination have not adequately provided success. Typically, if, after six months treatment with the present invention, improvement has not been shown, administration of growth hormones whould be instituted. In the advanced stages of the diseases, a growth hormone is also used at the outset of treatment, since, owing to its increased and magnified positive metabolic effect, a greater and more concentrated inducement of nerve cell regeneration is needed.

It is believed that the method of treatment of the present invention is successful for alleviating at least some symptoms for most patients in the incipient, beginning, or intermediate stages of the above-named diseases because of the following:

1. General increase in cerebral blood flow which enhances oxidation, including the normal metabolism of the brain cells;
2. Decrease of catabolism of protein and amino acids;
3. Enhancement of protein anabolism, leading to increased activity of brain cells, with the concomitant increase in red blood cell production;

4. Increase in the retention of calcium and sodium, which improve the axon-presynapticpostsynaptic cell transmission;
5. Increase of intercellular protein, which increases the formation of DNA and RNA;
6. The revitalization of the nerve cell body dendrite and axons of the pre-synaptic and post-synaptic cells.

It is, of course, to be understood that the dosage given during the use of the treatment of the present invention is dependent upon the weight, size, age, and the like, of the patient being treated. Further, any other well-known and equivalent sex hormone and anabolic hormone may be used in addition to those listed above, as long as the anabolic manifestations thereof are prevalent. Though the use of sex hormones, growth hormones, and anabolic hormones have been suspected of causing carcinoma, it is believed that in the doses abovestated for use in the treatment of the present invention, such likelihood is not of great probability. Further, since many of the patients for whom the present treatment would be useful and for whom it would prove successful, are quite advanced in age, and since their conditions are at present hopeless and their lives, for all intents and purposes, less than totally productive, it is believed that the beneficial and successful attributes of the treatment of the present invention far outweigh the possible negative side effects and hazards.

It has also been determined that, for female patients suffering from the above-named central nervous system degenerative diseases, the use of estradiol alone in suitable dosage provides sufficient anabolic effect, so that the use of an androgen supplemental to the female sex hormone is not needed. Estradiol has ample anabolic effect itself to preclude the need of the additional use of an androgen or anabolic hormone. The same holds true for the female gonadotropic sex hormones. Since gonadotropic sex hormones offer potent anabolic effects as well, the use of an androgen and/or anabolic hormone is not needed. However, owing to the relative lack of anabolic effect of conjugated estrogens and estrones, an androgen and/or anabolic hormone would be required in a female patient, when treating her with either a conjugated estrogen or estrone sex hormone. In advanced stages of the above-named degenerative diseases, the use of a gonadotropic female sex hormone is desirable, either alone or in combination with a growth hormone. The dosage, of course, will vary depending upon the age, size, and weight of the patient. The amount of initial dosage of gonadotropic hormone preferably is that dosage presently-used to treat pregnant women having low levels of these hormones, to prevent embrionic retardation.

What is claimed is:

1. The method for alleviating the symptoms of central nervous system diseases in a human being, said diseases being Parkinson's disease, cerebral atrophy, Alzheimer's disease, cerebellar atrophy, senile tremor, or essential tremor, comprising administering to said human being an effective amount of growth hormone and an androgen.

2. The method according to claim 1, further comprising administering the androgen before the treatment with said growth hormone.

3. The method according to claim 1, further comprising administering one from the following group: estradiol, estrone, estriol, and conjugated estrogen for a female patient, said one being administered for a period of time before said growth hormone is administered; said growth hormone being administered after said administration with said one of said group has proven unsuccessful.

4. The method according to claim 1, further comprising administering at least one of a gonadotropin and chorionic gonadotropin for female patients.

* * * * *